US011213637B2

(12) United States Patent
Fabien

(10) Patent No.: US 11,213,637 B2
(45) Date of Patent: Jan. 4, 2022

(54) DEVICE FOR INHALATION-SYNCHRONISED DISPENSING OF A FLUID PRODUCT

(71) Applicant: APTAR FRANCE SAS, Le Neubourg (FR)

(72) Inventor: David Fabien, Corseul (FR)

(73) Assignee: APTAR FRANCE SAS, Le Neubourg (FR)

(*) Notice: Subject to any disclaimer, the term of this patent is extended or adjusted under 35 U.S.C. 154(b) by 708 days.

(21) Appl. No.: 16/093,417

(22) PCT Filed: Apr. 13, 2017

(86) PCT No.: PCT/FR2017/050889
§ 371 (c)(1),
(2) Date: Oct. 12, 2018

(87) PCT Pub. No.: WO2017/178764
PCT Pub. Date: Oct. 19, 2017

(65) Prior Publication Data
US 2019/0134322 A1    May 9, 2019

(30) Foreign Application Priority Data

Apr. 15, 2016  (FR) ...................... 1653373

(51) Int. Cl.
*A61M 15/00*     (2006.01)
(52) U.S. Cl.
CPC ........ *A61M 15/009* (2013.01); *A61M 15/008* (2014.02); *A61M 15/0091* (2013.01);
(Continued)
(58) Field of Classification Search
CPC ............ A61M 15/009; A61M 15/0095; A61M 15/0091; A61M 15/0096; A61M 15/0093;
(Continued)

(56) References Cited

U.S. PATENT DOCUMENTS 3,456,646 A    7/1969  Phillips et al.
5,060,643 A *  10/1991 Rich ................. A61M 15/0091
                                              128/200.23
(Continued)

FOREIGN PATENT DOCUMENTS

NZ           562769 A       12/2010
WO      2004/028608 A1      4/2004
(Continued)

OTHER PUBLICATIONS

International Search Report of PCT/FR2017/050889 dated Jun. 26, 2017.
(Continued)

*Primary Examiner* — Kendra D Carter
*Assistant Examiner* — Thomas W Greig
(74) *Attorney, Agent, or Firm* — Sughrue Mion, PLLC

(57) ABSTRACT

A device including a body with a mouthpiece, a fluid reservoir mounted to slide relative to the body, a valve, a blocking element movable and/or deformable between a blocking position in which the metering valve cannot be actuated, and an actuation position in which the metering valve can be actuated; a trigger element movable and/or deformable between a locking position and a release position; and an inhalation-controlled trigger system. The blocking element including a projection that, in the locking position, co-operates with a shoulder of the trigger element to define a latch that prevents the blocking element from moving and/or deforming. The blocking element includes a lateral projection that, in the locking position of the trigger element, co-operates with a bearing surface of the trigger element to form, in the locking position of the trigger element, a second contact point between the blocking element and said trigger element.

13 Claims, 6 Drawing Sheets

(52) U.S. Cl.
CPC ............ *A61M 15/0095* (2014.02); *A61M 2205/3331* (2013.01); *A61M 2205/3553* (2013.01); *A61M 2205/3584* (2013.01); *A61M 2205/3592* (2013.01); *A61M 2205/502* (2013.01); *A61M 2205/52* (2013.01); *A61M 2205/8206* (2013.01)

(58) Field of Classification Search
CPC ............ A61M 15/0098; A61M 15/08; A61M 2205/3331; A61M 2205/3553; A61M 2205/3584; A61M 2205/3592; A61M 2205/502; A61M 2205/52; A61M 2205/8206
See application file for complete search history.

(56) References Cited

U.S. PATENT DOCUMENTS 5,119,806 A * 6/1992 Palson .............. A61M 15/0096
128/200.14
2002/0073992 A1 * 6/2002 Andersson ........ A61M 15/0091
128/200.23
2006/0243275 A1 * 11/2006 Ruckdeschel ........ A61M 11/001
128/200.23
2008/0156321 A1 * 7/2008 Bowman ........... A61M 15/0071
128/200.23

FOREIGN PATENT DOCUMENTS

| WO | 2008/070516 A2 | 6/2008 |
| WO | 2010/003846 A1 | 1/2010 |
| WO | 2013/178951 A1 | 12/2013 |

OTHER PUBLICATIONS

International Preliminary Report on Patentability with a Translation of Written Opinion in counterpart International Application No. PCT/FR2017/050889, dated Oct. 25, 2018.

* cited by examiner

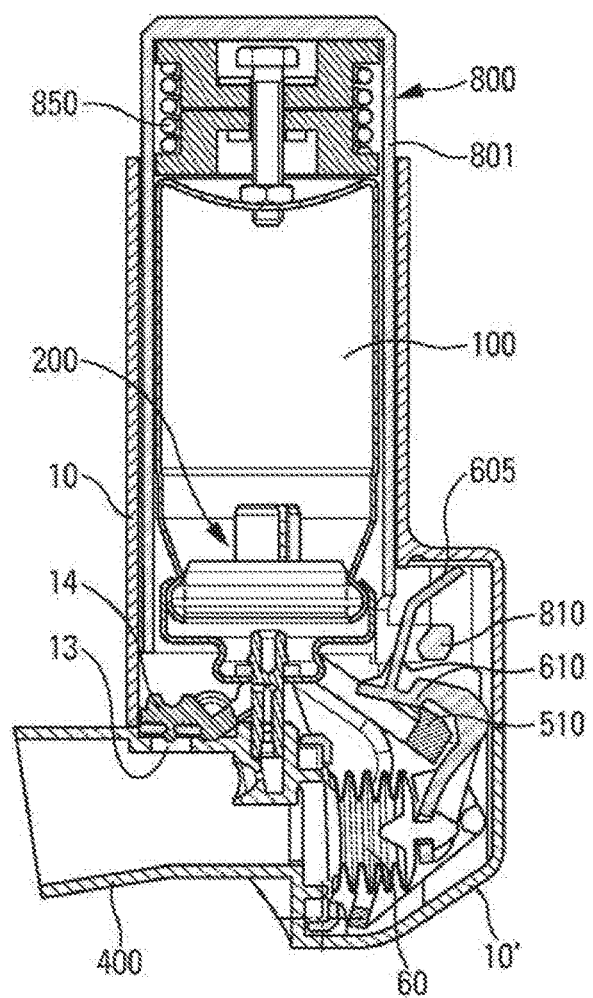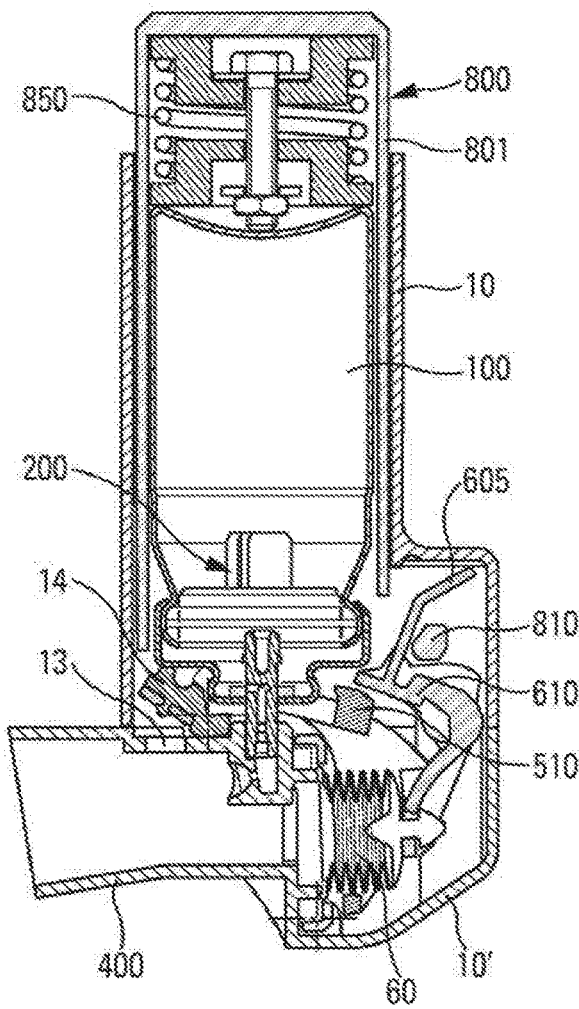
Fig. 3a
Fig. 4a
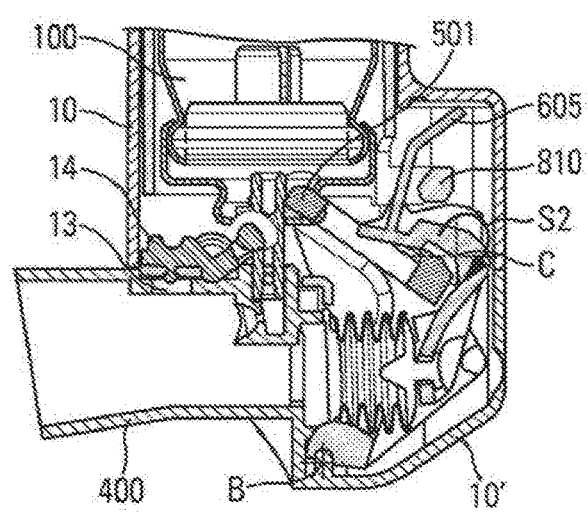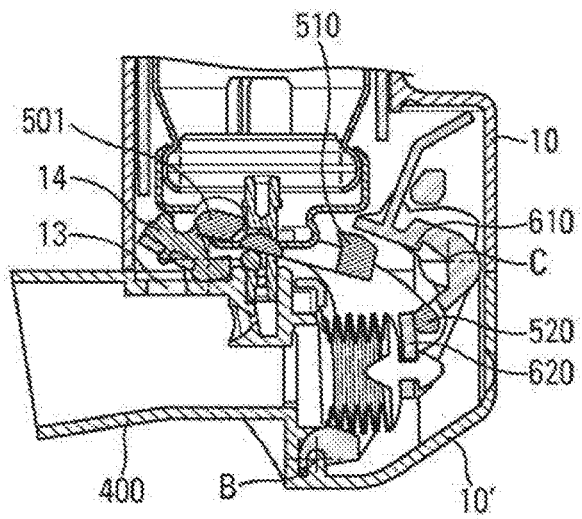
Fig. 3b
Fig. 4b

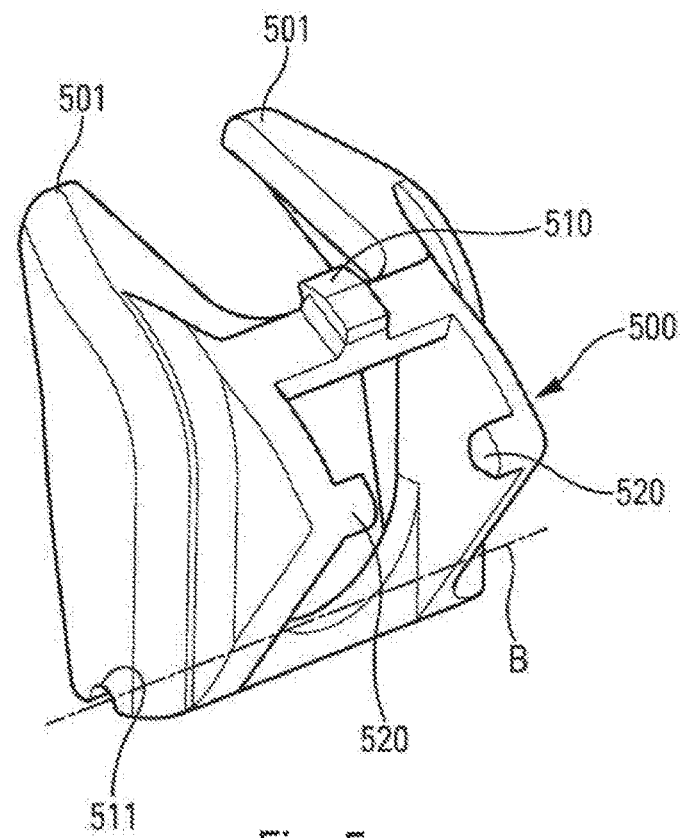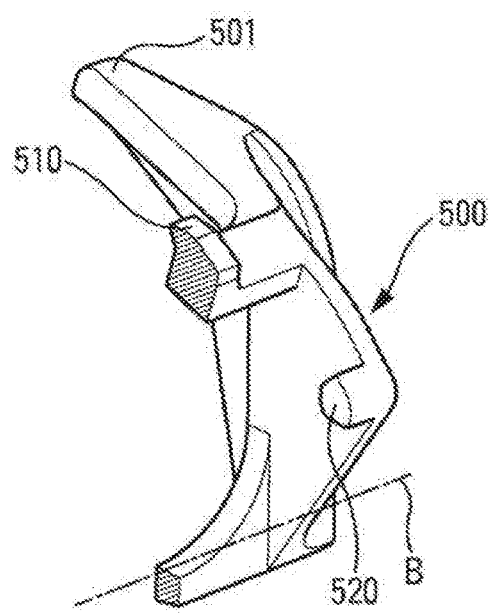
Fig. 5a Fig. 5b
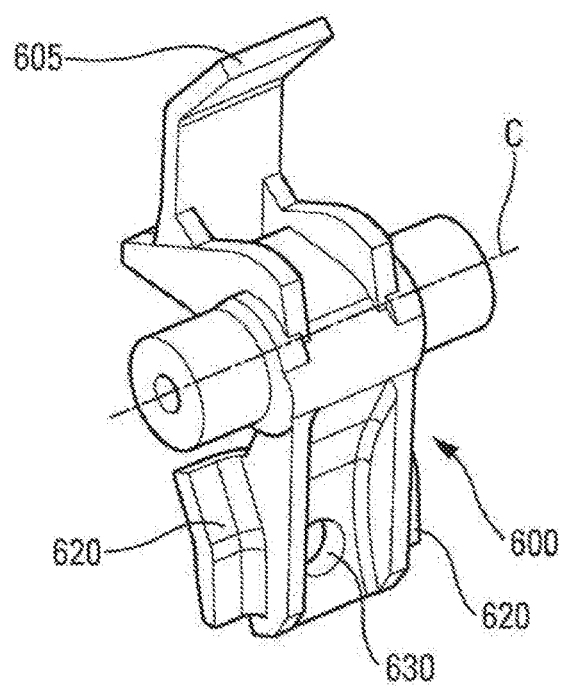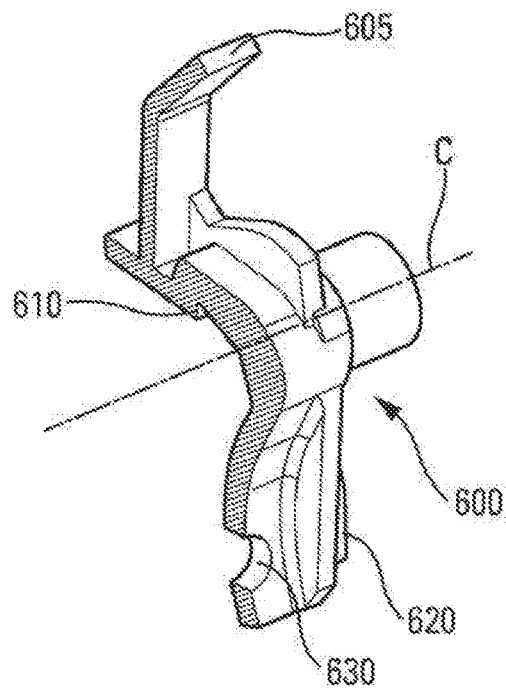
Fig. 6a Fig. 6b

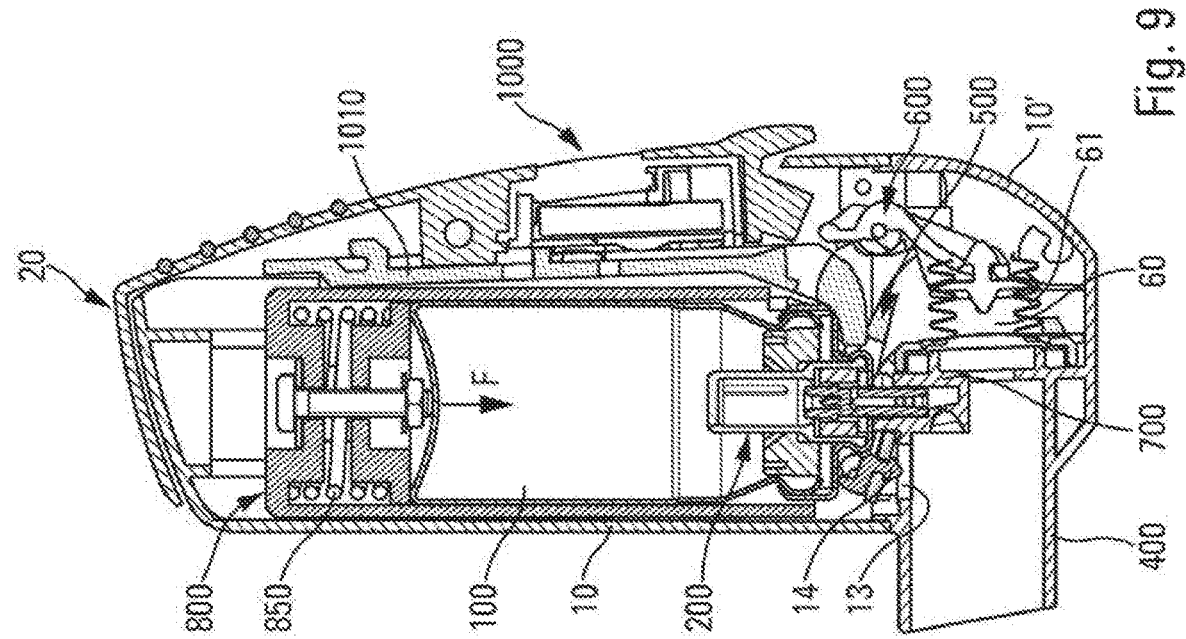
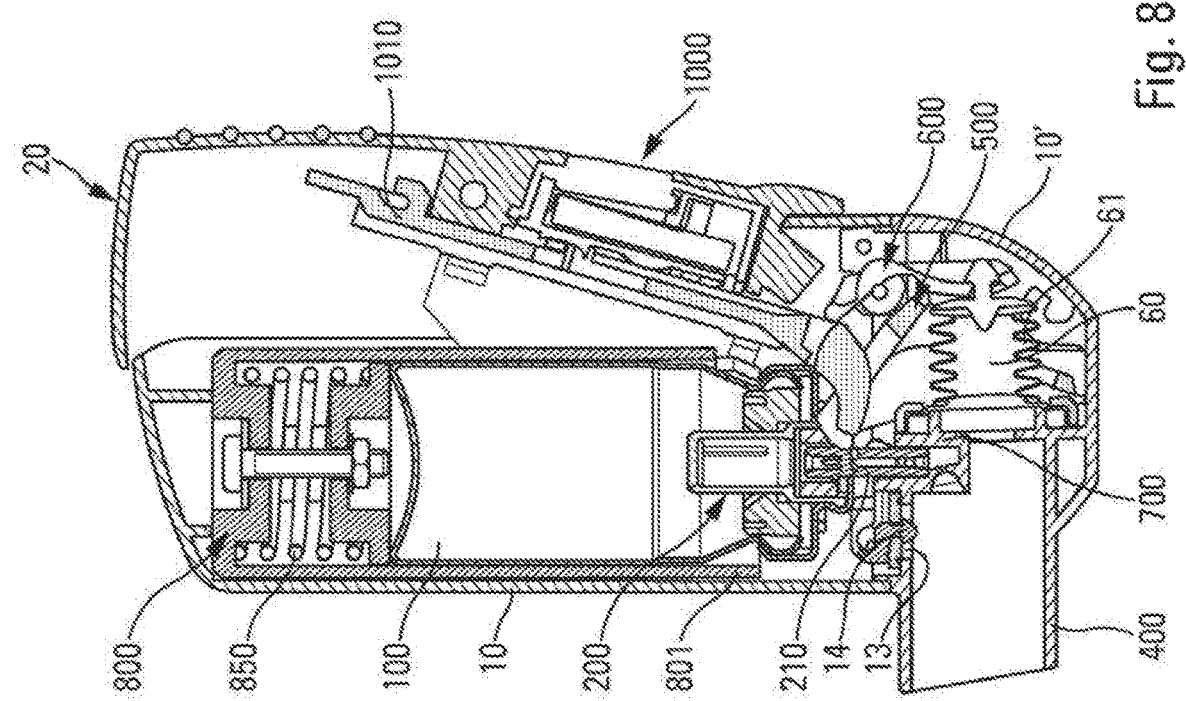

DEVICE FOR INHALATION-SYNCHRONISED DISPENSING OF A FLUID PRODUCT

CROSS REFERENCE TO RELATED APPLICATIONS

This application is a National Stage of International Application No. PCT/FR2017/050889 filed Apr. 13, 2017, claiming priority based on French Patent Application No. 1653373 filed Apr. 15, 2016.

The present invention relates to a fluid dispenser device in which dispensing is synchronized with inhaling, and more particularly it relates to an inhaler device of the aerosol type synchronized with inhaling.

Breath actuated inhaler (BAI) devices are well known in the state of the art. The main advantage of this type of device is that the dispensing of fluid is synchronized with the patient inhaling, so as to guarantee that the fluid is properly dispensed into the airways. Thus, in the field of aerosol devices, i.e. devices in which the fluid is dispensed by means of a propellant gas, numerous types of breath actuated inhaler device have been proposed. However, those devices present the drawback of including a large number of parts, i.e. they are complicated and costly to manufacture and to assemble, which is obviously disadvantageous. It is also difficult to find the right balance between reliable triggering on each inhalation, without the actuation threshold being too high, and a latch that is robust enough to prevent accidental of unwanted actuation. Unfortunately, when the latch releases accidentally, the device is actuated automatically and the dose is dispensed, even when the user does not want it.

Documents WO 2004/028608, U.S. Pat. Nos. 3,456,646, 5,119,806, NZ 562 769, US 2008/156321, WO 2008/070516, WO 2010/003846, and WO 2013/178951 describe prior-art devices.

An object of the present invention is to provide an inhalation-synchronized fluid dispenser device that does not have the above-mentioned drawbacks.

Another object of the present invention is to provide an inhalation-synchronized fluid dispenser device that improves operational reliability by guaranteeing effective actuation on each inhalation.

Another object of the present invention is to provide an inhalation-synchronized fluid dispenser device that minimizes the risks of accidental or unwanted actuation.

Another object of the present invention is to provide an inhalation-synchronized fluid dispenser device that does not present an actuation threshold that is too high, thereby making it possible for people who are relatively weak, such as the sick or the elderly, to use the device in safe and reliable manner.

Another object of the present invention is to provide an inhalation-synchronized fluid dispenser device that is simple and inexpensive to manufacture and to assemble.

The present thus provides an inhalation-synchronized fluid dispenser device comprising a body provided with a mouthpiece, a fluid reservoir containing a fluid and a propellant gas being mounted to slide axially relative to said body, a metering valve including a valve member being assembled on said reservoir for selectively dispensing the fluid, said device further comprising:

a blocking element that is movable and/or deformable between a blocking position in which said metering valve cannot be actuated, and an actuation position in which said metering valve can be actuated;

a trigger element that is movable and/or deformable between a locking position in which it blocks said blocking element in its blocking position, and a release position in which it does not block said blocking element; and an inhalation-controlled trigger system including an inhalation-sensitive member that is deformable and/or movable under the effect of inhaling, said inhalation-sensitive member co-operating with said trigger element, so that when said inhalation-sensitive member is deformed and/or moved, it moves and/or deforms said trigger element towards its release position, thereby making it possible to move and/or deform said blocking element from its blocking position towards its actuation position, said blocking element including a projection that, in the locking position of the trigger element, co-operates with a locking shoulder of said trigger element to define a latch that prevents said blocking element from moving and/or deforming out of its blocking position, said latch forming, in the locking position of the trigger element, a first contact point between said blocking element and said trigger element, said blocking element including a lateral projection that, in the locking position of the trigger element, co-operates with a bearing surface of said trigger element to form, in the locking position of the trigger element, a second contact point between said blocking element and said trigger element.

Advantageously, said blocking element is mounted to pivot on the body about an axis B, and said trigger element is mounted to pivot on the body about an axis C, said axes B and C being parallel.

Advantageously, in the locking position of the trigger element, said second contact point is at a distance from said axis C of the trigger element that is greater than the distance between said axis C and said first contact point.

Advantageously, an actuator member is assembled on the reservoir on the end that is axially remote from said metering valve, said actuator member comprising a hollow sleeve that is axially movable relative to said reservoir between a rest position and a primed position, a spring being arranged between the bottom of the reservoir and the closed top edge of said hollow sleeve, such that when the user presses manually on said actuator member so as to move it towards its primed position, said spring is compressed, so as to transmit an axial force F to said reservoir.

Advantageously, said actuator member includes a blocking tab, that co-operates in the rest position with said trigger element so as to prevent it from moving towards its release position.

Advantageously, a laterally-actuated pusher is mounted to pivot on the body between a rest position, and a working position in which it axially moves said actuator member into its primed position.

Advantageously, said inhalation-sensitive member includes a deformable membrane that defines a deformable air chamber, said deformable membrane being fastened to said trigger element, said deformable membrane being deformed during inhaling, so that it moves said trigger element from its locking position towards its release position.

Advantageously, said trigger element is accessible manually to the user, so that it can be moved manually towards its release position even in the absence of inhaling.

Advantageously, said body includes an opening that connects the mouthpiece to the inside of the body, said opening being closed at the start of inhaling by a check valve, such that the inhalation flow due to inhaling initially passes mainly to the trigger system.

Advantageously, said check valve is opened when said blocking element moves towards its actuation position.

Advantageously, said device includes an electronic dose counter.

Advantageously, said device includes signal-transmitter means for communicating, in particular communicating remotely, information relating to the actuations of the device.

These characteristics and advantages and others appear more clearly from the following detailed description, given by way of non-limiting example, and with reference to the accompanying drawings, in which:

FIG. 1b is view of a detail in FIG. 1a;

FIG. 2b is view of a detail in FIG. 2a;

FIG. 3a is a view similar to the view in FIG. 2a, shown after inhaling but before actuation;

FIG. 3b is view of a detail in FIG. 3a;

FIG. 4a is a view similar to the view in FIG. 3a, shown after actuation;

FIG. 4b is view of a detail in FIG. 4a;

FIG. 5a is a perspective view of the blocking element;

FIG. 5b is a cut-away view similar to the view in FIG. 5a;

FIG. 6a is a perspective view of the trigger element;

FIG. 6b is a cut-away view similar to the view in FIG. 6a;

FIG. 8 is a diagrammatic section view of a fluid dispenser device, in a second advantageous embodiment, in the rest position;

FIG. 9 is a view similar to the view in FIG. 8, shown after actuation; and

Figure 1A:
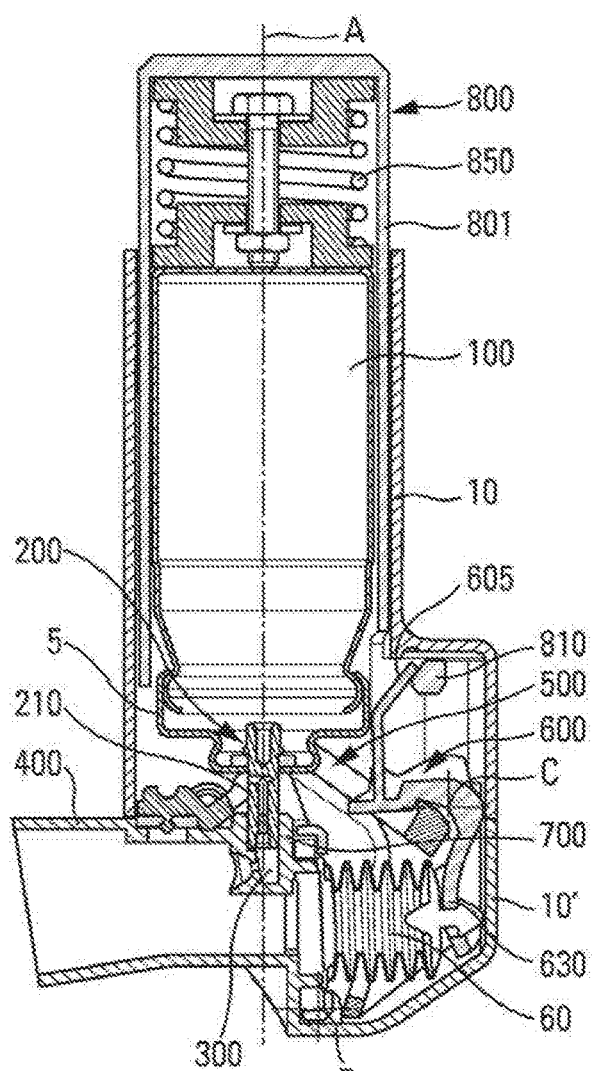
FIG. 1a is a diagrammatic section view of a fluid dispenser device, in a first advantageous embodiment, in the rest position.

In the description, the terms "top", "bottom", "upwards", and "downwards" refer to the upright position of the device shown in particular in FIG. 1a. The terms "axial" and "radial" are relative to the vertical central axis A shown in particular in FIG. 1a. The terms "proximal" and "distal" are relative to the mouthpiece.

The invention applies more particularly to inhaler devices of the aerosol-valve type for oral dispensing, as described in greater detail below, but it could also apply to other types of inhaler device, e.g. of the nasal type.

The figures show advantageous embodiments of the invention, but naturally one or more of the component parts described below could be made in some other way, while providing functions that are similar or identical.

With reference to the drawings, the device includes a main body 10 provided with a mouthpiece 400. The mouthpiece 400 defines a dispenser orifice through which the user inhales while the device is being used. The mouthpiece 400 may be made integrally with the body 10, but in the embodiments shown in the drawings, it is formed on a bottom body portion 10' that is fastened to said main body 10. A removable protective cap (not shown) may be provided on said mouthpiece 400, in particular while it is being stored, that the user removes before use.

The body 10 contains a reservoir 100 that contains the fluid to be dispensed and a propellant gas, such as a gas of the hydrofluoroalkane (HFA) type, a metering valve 200 being mounted on said reservoir 100 for selectively dispensing the fluid. The metering valve 200 comprises a valve body, and a valve member 210 that, during actuation, is axially movable relative to said valve body, and thus relative to said reservoir 100. The metering valve 200 can be of any appropriate type. It may be fastened to the reservoir 100 via a fastener element, preferably a crimped cap 5, preferably with a neck gasket interposed therebetween.

Advantageously, during actuation, the valve member 210 is stationary relative to the body 10, and it is the reservoir 100 that is moved axially relative to the body 10 between a distal position, which is the rest position, and a proximal position, which is the actuation position.

The outlet orifice of the valve member 210 of said metering valve 200 is connected via a channel 300 to said mouthpiece 400 through which the user inhales the fluid to be dispensed. In known manner, said valve member 210 is received in a valve well 700 that defines said channel 300, at least in part.

In the embodiment in FIGS. 1 to 7, an actuator member 800 is assembled on the top end of the reservoir 100, axially remote from said metering valve 200. The actuator member 800 comprises a hollow sleeve 801 that is arranged in the body 10 around the reservoir 100, with a spring 850 arranged between the bottom of the reservoir 100 and the closed top edge of said hollow sleeve 801. The hollow sleeve 801 is axially movable relative to said reservoir 100 between a rest position and a primed position. Thus, when the user wishes to move the reservoir 100 axially in the body 10, so as to actuate the metering valve 200, the user presses on said actuator member 800. This moves said hollow sleeve 801 axially towards its primed position and thus compresses said spring 850, which thus transmits an axial force F to said reservoir 100 which is substantially the same on each actuation. While the user continues to press on said actuator member 800, said spring 850 is compressed and drives said reservoir 100 axially towards its actuated position.

Figure 10:
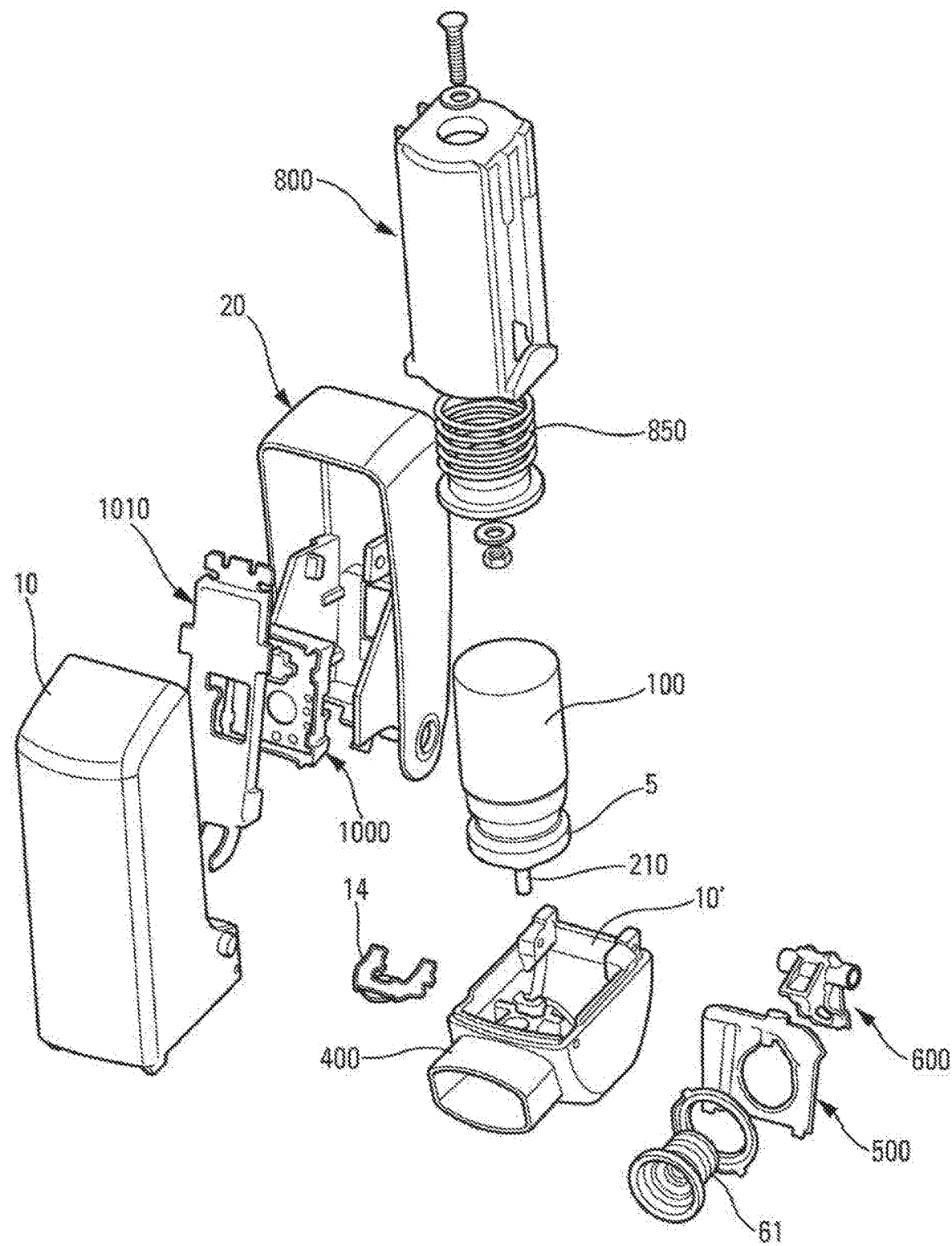
FIG. 10 is an exploded perspective view of the device in FIGS. 8 and 9.

FIGS. 8 to 10 show an advantageous variant, in which a laterally-actuated pusher 20 is mounted to pivot on the body 10. When moved from its rest position shown in FIG. 8, to its working position shown in FIG. 9, the pusher comes to move said actuator member 800 axially so as to compress the spring 850. In particular, this can be done by means of a cam on the pusher 20, that co-operates with a complementary profile on the actuator member 800. While the user continues to press on said pusher, said spring 850 is compressed and drives said reservoir 100 axially towards its actuated position. Advantageously, said pusher 20 includes a drive member that drives said pusher 20 towards its rest position. Thus, when the user relaxes the pressure on the pusher 20, said pusher returns automatically into its rest position. This makes it possible to avoid the risk, after actuating the metering valve 200, of said metering valve remaining in its actuated position, which could cause the valve chamber to fill with air and the following dose to be incomplete, or it could cause the valve to leak. This is one of the problems that currently exists with devices that are currently on the market.

In the invention, the device includes a blocking element 500 that is movable and/or deformable between a blocking position in which said metering valve 200 cannot be actuated, and an actuation position in which said metering valve 200 can be actuated. In the rest position, said blocking element 500 is in the blocking position, and it is the user inhaling through the mouthpiece 400 that moves and/or deforms said blocking element 500 towards its actuation position. In other words, so long as the user does not inhale, it is impossible to actuate the metering valve 200, and it is only when the user inhales that said metering valve 200 can be actuated, advantageously by pressing manually on an actuation member 800 that co-operates with the bottom of the reservoir 100.

As described in greater detail below, the blocking element 500, in its blocking position, prevents the reservoir 100 from moving axially in the body 10. During inhaling, the blocking element 500 is moved and/or deformed so that it no longer prevents the reservoir 100 from moving axially in the body 10. Thus, after inhaling, such axial movement of the reservoir 100 causes the metering valve 200 to be actuated and a dose of fluid to be dispensed, synchronously with the inhaling.

Thus, in the absence of inhaling, there is no risk of an active dose of fluid being lost by accidental or incomplete actuation during which the user does not inhale. Actuating the valve 200 and expelling a dose of fluid are thus possible only when the user inhales and simultaneously presses axially on the reservoir 100 so as to actuate the valve 200. As described above, it is possible to press axially on the reservoir 100 by means of the actuator member 800 that compresses the spring 850. In a variant, the user could press directly on the bottom of the reservoir 100. In the variant in FIGS. 8 to 10, it is the pusher 20 that generates the axial pressure, also via the actuator member 800 in the embodiment shown. Finally, it is also possible to use an automatic actuator system that would apply the axial pressure on the reservoir 100 independently of the user.

The device includes a trigger system that is controlled by the user inhaling, and that is for moving and/or deforming said blocking element 500 from its blocking position towards its actuation position, when the user inhales through the mouthpiece 400.

The trigger system includes an inhalation-sensitive member 60 that is deformable and/or movable under the effect of inhaling, the inhalation-sensitive member 60 being adapted, when it is deformed and/or moved, to make it possible to move and/or deform said blocking element 500 from its blocking position towards its actuation position.

As described in greater detail below, the inhalation-sensitive member may be made in the form of a deformable air chamber 60, e.g. a bellows or a deformable pouch.

FIGS. 1 to 7 show a first embodiment of the invention.

The blocking element 500 is advantageously mounted to pivot about an axis B on the body 10, or on the body portion 10', between a blocking position and an actuation position. In the embodiment shown, said axis B passes via a bottom edge of said blocking element 500. It may be formed by projections 11' that are provided on a bottom surface of the body portion 10', the blocking element 500 including complementary profiles 511 that are adapted to pivot on said projections 11'. Other embodiments are also possible.

The blocking element 500 includes at least one, preferably two, blocking extensions 501, that co-operate in the blocking position with the reservoir 100 (advantageously with the crimping cap 5). FIGS. 5a and 5b show a perspective view and a cut-away perspective view of the blocking element 500.

The blocking element 500 is held in its blocking position by a trigger element 600. FIGS. 6a and 6b show a perspective view and a cut-away perspective view of the trigger element 600. The trigger element 600 is mounted to pivot about an axis C on the body 10, on the body portion 10', or on the pusher 20, between a locking position in which it blocks said blocking element 500 in its blocking position, and a release position in which it no longer blocks said blocking element 500. In the embodiment shown, said axis C passes approximately in the middle of said element of said trigger element 600. Advantageously, the axes B and C are parallel.

The blocking element 500 and the trigger element 600 co-operate with each other to define a latch. In particular, said trigger element 600 includes a locking shoulder 610 that, in the locking position, co-operates with a projection 510 of the blocking element 500, preventing said blocking element 500 from pivoting out of its blocking position. Thus, when said trigger element 600 is in its locking position, it prevents the blocking element from moving towards its actuation position, thereby preventing the reservoir 100 from moving axially and the metering valve 200 from thus being actuated.

The latch makes it possible to unlock a large force (typically about 40 newtons (N) to 45 N) by means of a small force generated by inhaling. The blocking element 500 stops the can from moving in translation when it is subjected to a force F (e.g. of 45 N) by means of the user pressing on the actuator member 800. The blocking element 500 interacts with the trigger element 600, and it is both blocked and released by said trigger element. The movement of said trigger element 600 is controlled by inhaling.

The shape of the latch enables very large amplification (locked force/unlocked force), typically of about 100.

In the invention, the blocking element 500 and the trigger element 600 have two contact points that are spaced apart:
- a first contact point, formed by the latch defined between the locking shoulder 610 and the projection 510, is advantageously situated close to the pivot axis C of the trigger element 600;
- a second contact point at a distance from the first contact point, formed by the co-operation between a lateral projection 520 of the blocking element 500 and a bearing surface 620 of the trigger element 600; advantageously, in the locking position, the second contact point is at a distance from the axis C of the trigger element 600 that is greater than the distance between said axis C and the first contact point; advantageously, the second contact point is the first contact that is broken while actuating the device, when the user begins to inhale.

In the blocking position, the force F generated by pressing axially on the reservoir 100 is applied to the blocking element 500 at the extensions 501, causing it to turn in a direction S1 that reinforces the closed position of the latch and makes it stable.

The unlocking force generated by inhaling is applied to the trigger element 600 by the deformable membrane 61, preferably at a point 630 at a distance from the pivot axis C; the unlocking force seeks to turn said trigger element 600 in the direction S2 opposite to the direction S1.

The torque to which the blocking element 500 is subjected is controlled by the distance between the axis along which the force F is applied to the blocking extensions 501 of the blocking element, and the pivot axis B of said blocking element 500. It is desirable for the distance to be as small as possible, in order for the torque to be as small as possible.

The torque to which the trigger element 600 is subjected is controlled by the distance between the axis conveying the force F' to which the trigger element 600 is subjected by the blocking element 500, and the pivot axis C of said trigger element 600. Once again, it is desirable for the distance to be as small as possible, in order for the torque to be as small as possible.

Figure 2A:
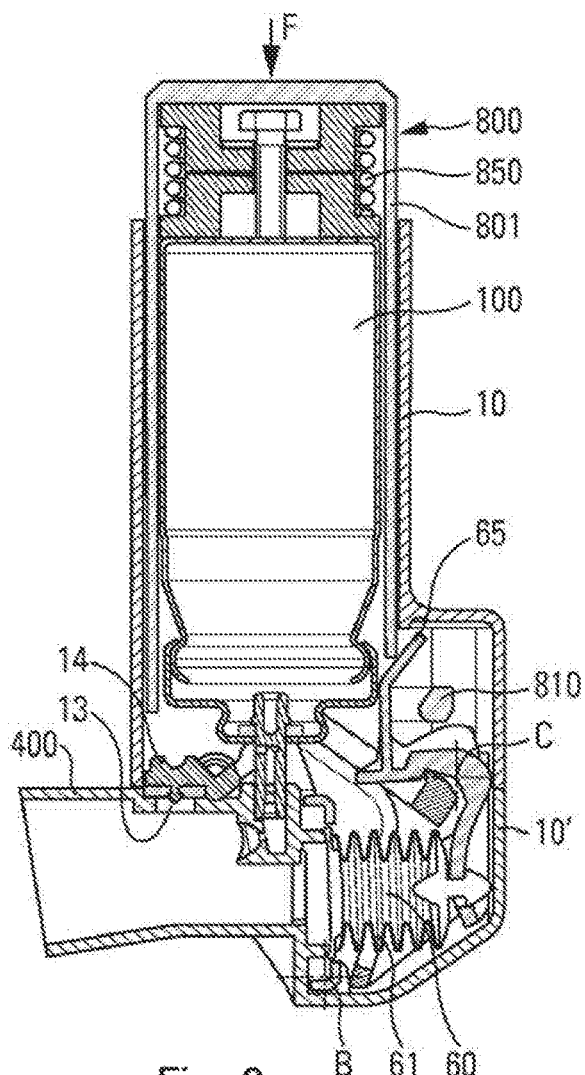
FIG. 2a is a view similar to the view in FIG. 1a, after pressing on the reservoir but before inhaling.
Figure 1B:
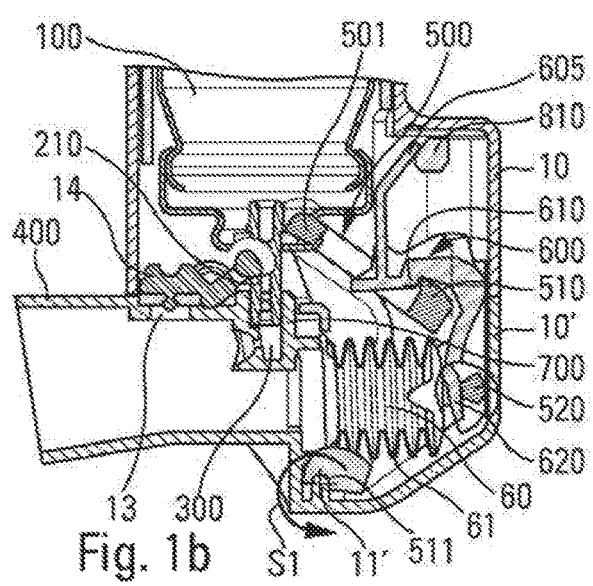
Figure 2B:
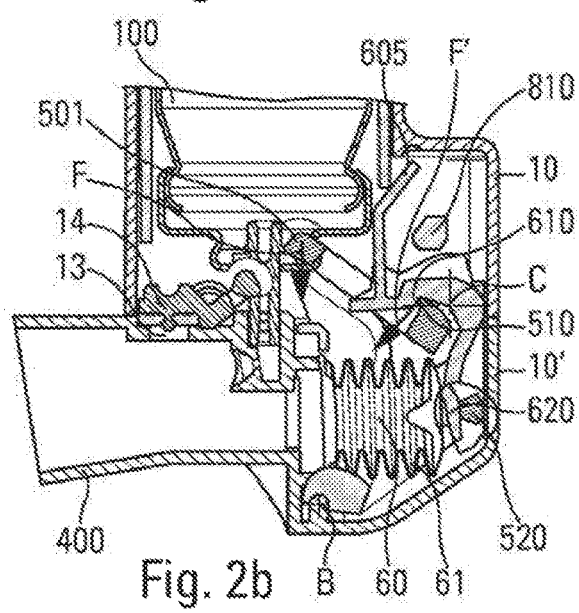
Figure 7:
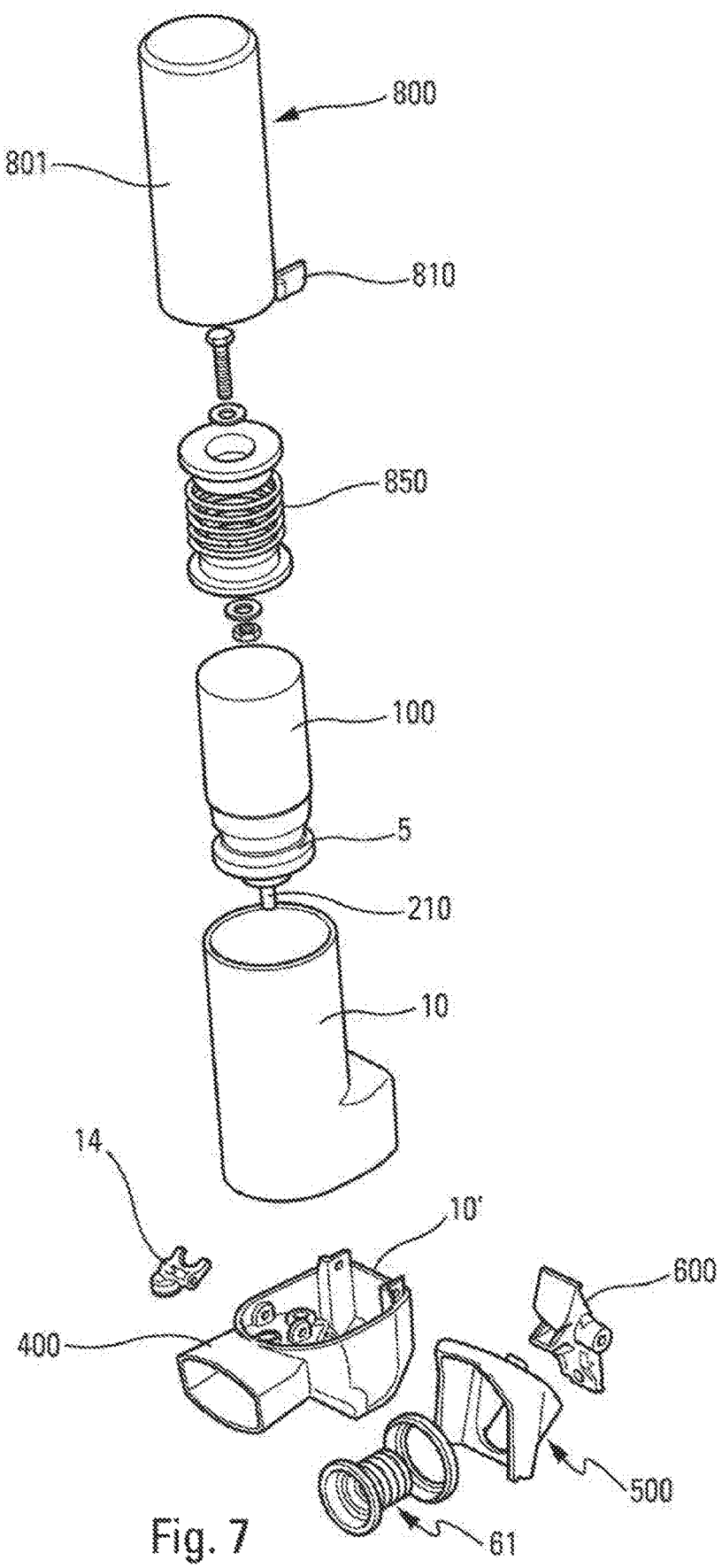
FIG. 7 is an exploded perspective view of the dispenser in FIGS. 1 to 6.

FIG. 2b shows the two forces F and F'.

By means of this latch force system, the force necessary to cause the trigger element 600 to pivot is very small and may be generated by the deformable membrane 61, that makes it possible to transform the suction generated by inhaling into unlocking force.

Advantageously, the bottom body portion 10' includes an opening 13 that is connected to the inside of the body 10. The opening 13 is closed at rest and at the start of inhaling by a check valve 14, so that the inhalation flow due to inhaling initially passes mainly to the trigger system, in this embodiment the deformable air chamber 60. This makes it possible to optimize such triggering by inhaling. When the blocking element 500 is moved towards its actuation position under the effect of inhaling, and thus when the user can actuate the metering valve 200 so as to dispense a dose of fluid, said blocking element 500 moves said check valve 14 towards an open position. When said openings 13 are thus open, air is drawn in, thereby making it possible to increase the inhalation flow. This optimizes synchronization between the user inhaling and dispensing the dose, and also promotes good dispensing of the dose into the user's lungs.

Advantageously, the trigger element 600 may be accessible from the outside of the body 10 and/or of the bottom body portion 10'. This makes it possible, if necessary, to move the trigger element 600 manually, so as to be able to actuate the metering valve 200 even without inhaling, e.g. when the person that needs to receive the dose of fluid is incapable of inhaling sufficiently. This is thus a safety measure.

In the embodiments shown in the figures, the inhalation-sensitive member 60 is made in the form of a deformable air chamber. Advantageously, the air chamber comprises a deformable membrane 61 that is connected firstly to said bottom body portion 10' and secondly to said trigger element 600. Advantageously, as can be seen in the figures, the membrane 61 is in the form of a bellows and forms a substantially airtight chamber. Other forms are possible, in particular a mere pouch or diaphragm. A lug may fasten said membrane 61 to an orifice 630 of said trigger element 600.

During inhaling, the deformable membrane 61 deforms and/or contracts under the effect of the suction generated by inhaling, causing the trigger element 600 to move from its locking position towards its release position. This makes it possible to open the latch defined between the blocking element 500 and the trigger element 600, and thus to move said blocking element 500 from its blocking position towards its actuation position.

The valve 200 is thus actuated only at the moment of inhaling, such that the dose of fluid is expelled out of the dispenser orifice simultaneously with inhaling.

Advantageously, the actuator member 800 includes a blocking tab 810, that co-operates in the rest position with said trigger element 600, in particular a locking tab 605, so as to prevent said trigger element from moving towards its release position. Thus, when the user inhales without having pressed axially on the reservoir 100, the latch is not unblocked, since the trigger element 600 cannot pivot. Since the air chamber 60 is substantially airtight, and the check valve 14 is closed in the opening 13, the user very quickly realizes that it is not possible to inhale correctly through the mouthpiece, which reminds the user that it is necessary to exert axial pressure on the reservoir 100 first before inhaling. When the user presses on the actuator member 800, the sleeve 801 is moved axially relative to the reservoir 100, which is itself blocked by the blocking element 500, and this compresses the spring 850. The axial movement of the sleeve 801 releases the interaction between the locking tab 605 of the trigger element 600 and the blocking tab 810, as can be seen in FIGS. 2a and 2b. Inhaling thus causes the trigger element 600 to pivot, and thus causes the device to be actuated, as explained above.

When the user wishes to use the device, the user places the mouthpiece 400 in the mouth, and exerts axial pressure manually on the bottom of the reservoir 100, i.e. the top surface of said reservoir 100 in the position in the figures. The reservoir 100 is blocked and prevented from sliding axially in the body 10 by the blocking extensions 501 of the blocking element 500. Simultaneously, the trigger element 600 is no longer blocked as a result of the axial movement of the actuator member 800, as can be seen in FIGS. 2a and 2b.

When the user inhales through the mouthpiece 400, the deformable membrane 61 deforms, and this causes the trigger element 600 that is fastened to said deformable membrane 61 to pivot. The movement of the trigger element 600 releases the latch formed between the locking shoulder 610 of the trigger element 600 and the projection 510 of the blocking element 500, as can be seen in FIGS. 3a and 3b. Under the effect of the axial force transmitted by the reservoir 100, generated by pressing axially on the bottom of said reservoir 100, the blocking element 500 pivots enabling the reservoir 100 to slide axially in the body 10 towards its dispensing position, and the valve 200 thus to be actuated. Simultaneously, the blocking element 500 opens the check valve 14. This dispensing position is shown in FIGS. 4a and 4b.

At the end of inhaling, when the user releases the pressure on the bottom of the reservoir 100, said reservoir rises axially in the body towards its rest position under the effect of the return spring of the valve 200, and the valve member 210 of the metering valve simultaneously returns to the rest position, once again filling the valve chamber with a new dose of fluid. The trigger element 600 is returned into its initial position by the springiness of the membrane 61 and/or by the blocking tab 810 of the actuator member 800 that returns towards its rest position. The blocking element 500 returns into its blocking position, advantageously via a resilient element, such as a spring or an element made of elastomer (not shown).

The device is thus ready for another utilization.

FIGS. 8 to 10 show a variant embodiment that, in particular, includes the above-mentioned laterally-actuated pusher 20 and that includes electronic modules.

In particular, an electronic dose counter 1000 is provided, advantageously assembled in the pusher 20. In particular, the counter 1000 may detect the movements of the reservoir 100, e.g. by means of a slider 1010 that is moved by the reservoir 100 or by the blocking element 500, when they arrive in the dispensing position. In a variant, the counter 1000 could be connected to a sensor, in particular a membrane sensor, that detects the dose of fluid being dispensed, e.g. in the valve well 700. The electronic counter 1000 may be actuated in other ways, e.g. by detecting the movement of the valve member 210 of the metering valve relative to the valve body.

Preferably, the device also includes signal-transmitter means for communicating, in particular communicating remotely, information relating to the actuations of the device. In particular, the body 10 and/or the pusher 20 may include a signal-transmitter module, for communicating remotely with any base. Appropriate power supply means are advantageously provided.

In particular, the electronic module may advantageously comprise a card that includes an electrical switch that sends a pulse. The module may also comprise a display and/or use a Bluetooth or Wifi connection for sending information to an accompanying peripheral. Appropriate sensors, such as flowrate and/or pressure sensors, may be provided for detecting various parameters of the inhalation flow.

The switch may be actuated by the movement of the blocking element 500, either directly, or via the slider shown in the figures.

In the embodiment shown, the electronic module and its associated slider are positioned in the pusher 20, movable relative to the body 10. But, in a variant, it is possible to envisage a module that is stationary relative to the body 10.

Associated with a dose counter that counts each dose that is actually dispensed, and with the inhalation-synchronized device of the invention, the signal-transmitter means make it possible for each dose that has been dispensed to be transmitted in completely reliable manner, e.g. to a doctor or to any other person wishing to monitor the use of the inhaler device by the user. The inhalation-synchronized device guarantees that the user inhales each time the user actuates the device, and the counter records each dose that is dispensed, together with various associated parameters, such as a timestamp for each dispensing. In this way, the doctor can know very accurately the conditions of use of the device by the user.

The present invention applies, in particular, to treating asthma attacks or chronic obstructive pulmonary disease (COPD), by using formulations of the following types: salbutamol, aclidinium, formoterol, tiotropium, budesonide, fluticasone, indacaterol, glycopyrronium, salmeterol, umeclidinium bromide, vilanterol, olodaterol, or striverdi, or any combination of these formulations.

The present invention is described above with reference to advantageous embodiments and variants, but naturally any modification could be applied thereto by a person skilled in the art, without going beyond the ambit of the present invention, as defined by the accompanying claims.

The invention claimed is:

1. An inhalation-synchronized fluid dispenser device comprising a body provided with a mouthpiece, a fluid reservoir containing a fluid and a propellant gas being mounted to slide axially relative to said body, a metering valve including a valve member being assembled on said reservoir for selectively dispensing the fluid, said device further comprising:
    a blocking element that is movable and/or deformable between a blocking position in which said metering valve cannot be actuated, and an actuation position in which said metering valve can be actuated;
    a trigger element that is movable and/or deformable between a locking position in which it blocks said blocking element in the blocking position, and a release position in which it does not block said blocking element; and
    an inhalation-controlled trigger system including an inhalation-sensitive member that is deformable and/or movable under the effect of inhaling, said inhalation-sensitive member co-operating with said trigger element, so that when said inhalation-sensitive member is deformed and/or moved, it moves and/or deforms said trigger element towards the release position, thereby making it possible to move and/or deform said blocking element from the blocking position towards the actuation position;
the device being characterized in that said blocking element includes a projection that, in the locking position of the trigger element, co-operates with a locking shoulder of said trigger element to define a latch that prevents said blocking element from moving and/or deforming out of the blocking position, said latch forming, in the locking position of the trigger element, a first contact point between said blocking element and said trigger element, said blocking element including a lateral projection that, in the locking position of the trigger element, co-operates with a bearing surface of said trigger element to form, in the locking position of the trigger element, a second contact point between said blocking element and said trigger element.

2. A device according to claim 1, wherein said blocking element is mounted to pivot on the body about an axis B, and said trigger element is mounted to pivot on the body about an axis C, said axes B and C being parallel.

3. A device according to claim 2, wherein, in the locking position of the trigger element, said second contact point is at a distance from said axis C of the trigger element that is greater than the distance between said axis C and said first contact point.

4. A device according to any preceding claim 1, wherein an actuator member is assembled on the reservoir on the end that is axially remote from said metering valve, said actuator member comprising a hollow sleeve that is axially movable relative to said reservoir between a rest position and a primed position, a spring being arranged between the bottom of the reservoir and the closed top edge of said hollow sleeve, such that when the user presses manually on said actuator member so as to move it towards the primed position, said spring is compressed, so as to transmit an axial force to said reservoir.

5. A device according to claim 4, wherein said actuator member includes a blocking tab, that co-operates in the rest position with said trigger element so as to prevent said trigger element from moving towards the release position.

6. A device according to claim 4, wherein a laterally-actuated pusher is mounted to pivot on the body between the rest position, and a working position in which it axially moves said actuator member into the primed position.

7. A device according to claim 1, wherein said inhalation-sensitive member includes a deformable membrane that defines a deformable air chamber, said deformable membrane being fastened to said trigger element, said deformable membrane being deformed during inhaling, so that it moves said trigger element from the locking position towards the release position.

8. A device according to claim 1, wherein said trigger element is accessible manually to the user, so that it can be moved manually towards the release position even in the absence of inhaling.

9. A device according to claim 1, wherein said body includes an opening that connects the mouthpiece to the inside of the body, said opening being closed at the start of inhaling by a check valve , such that the inhalation flow due to inhaling initially passes mainly to the trigger system.

10. A device according to claim 9, wherein said check valve is opened when said blocking element moves towards the actuation position.

11. A device according to claim 1, including an electronic dose counter.

12. A device according to claim 1, including signal-transmitter means for communicating information relating to the actuations of the device.

13. A device according to claim 12, wherein the signal-transmitter means remotely communicates information relating to the actuations of the device.

\* \* \* \* \*